US005671848A

United States Patent [19]
Cohen et al.

[11] Patent Number: 5,671,848
[45] Date of Patent: Sep. 30, 1997

[54] KIT FOR THE DIAGNOSIS OF INSULIN DEPENDENT DIABETES MELLITUS

[75] Inventors: Irun Robert Cohen; Dana Elias, both of Rehovot; Doron Markovits, Gedera, all of Israel

[73] Assignee: Yeda Research and Development Co. Ltd., Rehovot, Israel

[21] Appl. No.: 39,704

[22] Filed: Mar. 29, 1993

Related U.S. Application Data

[62] Division of Ser. No. 848,517, Mar. 9, 1992, abandoned, which is a division of Ser. No. 371,249, Jun. 26, 1989, Pat. No. 5,114,844, which is a continuation-in-part of Ser. No. 322,864, Mar. 24, 1989, abandoned.

[51] Int. Cl.$^6$ ..................................................... G01N 33/53
[52] U.S. Cl. .......................... 206/569; 435/7.1; 435/7.9; 435/7.92; 530/350; 530/868
[58] Field of Search ........................... 424/88, 92, 184.1, 424/185.1, 248.1; 514/2, 866; 530/350, 868; 435/7.1–7.2, 7.32, 7.9, 7.92; 436/506, 518, 512, 810, 811; 206/569

[56] References Cited

U.S. PATENT DOCUMENTS 5,114,844  5/1992  Cohen et al. ........................... 435/7.21

FOREIGN PATENT DOCUMENTS

| 0261648 | 12/1987 | European Pat. Off. . |
| 0262710 | 4/1988 | European Pat. Off. . |
| 0262710 | 6/1988 | European Pat. Off. ........ A61K 37/02 |
| 0333606 | 2/1989 | European Pat. Off. . |
| 8806591 | 9/1988 | WIPO ............................ C07H 15/12 |

OTHER PUBLICATIONS

Atkinson, Mark A., et al., Lancet 336:1250–1251 (Nov. 17, 1990), "No role for the 65 kD heat-shock protein in diabetes".

Jones, David B., et al. Lancet 337:115 (Jan. 12, 1991), "Is there no role for heat-shock protein in diabetes?".

Kämpe, Olle, et al., Lancet 336:1250 (Nov. 17, 1990), "No role for 65 kD heat-shock protein in diabetes".

Latchman, David, Nature 356;114 (Mar. 12, 1992), "No diabetes link to hsp65?".

Lydyard, Peter, et al., Immunology Today 11(7):228–9 (1990), "Heat shock proteins: immunity and immunopathology".

G.M. Bahr et al, Clin. Exp. Immunol., 74, 211–215, 1988.

G. Tsoufla et al, Ann. Rheum. Dis., 48, 118–123, 1989.

S. Jindal et al, "Primary structure of a human mitochondrial protein homologous to the bacterial and plant chaperonins and to the 65–kilodalton mycobacterial antigen", Molec. Cell. Biol., 9, 2279–2283, 1989.

S. Baekkeskov et al, Nature, 298, 167–169, 1982.

S. Baekkeskov et al, Nature, 347, 151–156, 1990.

Bahr, G. M., et al., Clin. Exp. Immunol. 74:211–215 (1988), "Antibody levels to mycobacteria in relation to HLA type: evidence for non–HLA–linked high levels of antibody to the 65 KD heat shock protein of M. bovis in rheumatoid arthritis".

Rook, G. A.W., Scand. J. Immunol. 28:487–493 (1988), "Rheumatoid arthritis, mycobacterial antigens and agalactosyl IgG".

Thole, J. E. R. et al., Infect. Immun. 50:800–806 (1985), "Cloning of Mycobacterium bovis BCG DNA and expression of antigens in E. coli".

S. Baekkeskov et al. "Autoantibodies in newly diagnosed diabetic children immunoprecipitate human pancreatic islet cell proteins", Nature, 298: 167–169, 1982.

S. Baekkeskov et al., "Identification of the 64K autoantigen in insulin–dependent diabetes as the GABA–synthesizing enzyme glutamic acid decarboxylase", Nature, 347: 151–156, 1990.

M. Bahr et al., "Antibody levels to mycobacteria in relation to HLA type: evidence for non–HLA–linked levels of antibody to the 65 kD heat shock protein of M.bovis in rheumatoid arthritis", Clin. Exp. Immunol., 74: 211–215, 1988.

S. Jindal et al., "Primary Structure of a Human Mitochondrial Protein Homologous to the Bacterial and Plant Chaperonins and to the 65–Kilodalton Mycobacterial Antigen", Molecular and Cellular Biology, 9(5): 2279–2283, 1989.

G. Tsoufla et al., "Raised serum IgG and IgA antibodies to mycobacterial antigens in rheumatoid arthritis", Ann. Rheum. Dis., 48: 118–123, 1989.

D. Elias et al., "Induction and therapy of autoimmune diabetes in the nonobese disbetic (NOD/Lt) Mouse by a65–kDa heat shock protein", PNAS, 87: 1990.

J. Thole et al., "Characterization, Sequence Determination, and Immunogenicity of a 64–Kilodalton Protein of Mycobacterium bovis BCG Expressed in Escherichia coli K–12", Infection and Immunity, 55(6): 1466–1475, 1987.

Cohen, Irun R., "The Self, the World and Autoimmunity", Scientific American, 256: 52–60, 1988.

Thole et al., "Characterization, Sequence Determination, and Immunogenicity of a 64–Kilodalton Protein of Mycobacterium bovis BCG Expressed Escherchia coli K–12", Infection and Immunity, 55(19):.

Minota et al., "Autoantibodies to the Heat–Shock Protein hsp90 in Systemic Lupus Erythematosus", J. Clin. Invest., 81: 106–109, 1988.

(List continued on next page.)

Primary Examiner—Thomas M. Cunningham
Attorney, Agent, or Firm—Browdy and Neimark

[57] ABSTRACT

A 65 KD heat shock protein, proteins cross-reactive therewith, or antibodies thereto can be used for detecting in humans the existence of, a tendency to develop, or the initiation of a process leading to insulin dependent diabetes mellitus. Antibodies to hsp65 can be used to detect the hsp65 molecule in blood or urine. The hsp65 molecule of any species, or any other substance immunologically cross-reactive therewith, when administered with a tolerogenic carrier, can be used for the prevention or treatment of IDDM prior to development of clinical symptoms thereof.

13 Claims, 4 Drawing Sheets

OTHER PUBLICATIONS

Res et al., "Synovial Fluid T Cell Reactivity Against 65 kD Heat Shock Protein of Mycobacteria in Early Chronic Arthritis", *The Lancet*, 478–480, 1988.

Vandenbark et al., "Immunization with a synthetic T-cell receptor V-region peptide protects against experimental autoimmune encephalomyelitis", *Nature*, 341: 541–544, 1989.

Howell et al., "Vaccination Against Experimental Allergic Encephalomyelitis with T Cell Receptor Peptides", *Science*, 246: 668–670, 1989.

Borek, F., "Immunogenicity", ed. North–Holland Publishing Co., Amsterdam, 1972; chapters 3 and 4.

Rossini et al., "Immunology of Insulin–Dependent Diabetes Mellitus", *Ann. Rev. Immunol.* 3:289–320 (1985).

Van Eden et al., "Cloning of the mycobacterial epitope recognized by T lymphocytes in adjuvant arthritis", *Nature* 331:171–173 (1988).

N.R. Rose, in *Basic and Clinical Immunol.* (1980) pp. 644, 654–656.

I.R. Cohen, Ann. Rev. Immunol. 9:567–89. (1991) "Autoimmunity to chaperonins in the Pathogenesis of Arthritis and Diabetes".

Fig. 3A

```
-45  GACGACCTGTCTCGCGAGCGCACGCTTTGCGCGCCCCGAGAAATGCTTCGGTTACCACAGTCTTTGCCAGATGAGACCGGTGTCC
      D  D  L  S  R  R  A  H  A  C  R  R  P  A  E  MetLeuArgProThrValPheArgGlnMetArgProValSer  15

46  AGGGTACTGGCTCCTCCTCATCTCACTCGGGCTTATGCGAAAGATGTAAAATTGGTGCAGATGCCCGAGCCTTAATGCTTCAAGGTGTAGAC
      ArgValLeuAlaProHisLeuThrArgAlaLeuThrArgAlaLeuAlaTyrAlaLysAspValLysPagGlyAlaAspAlaArgAlaLeuMetLeuGlnGlyValAsp  45

136  CTTTTAGCCGATGCTGTGGCCGTTACAATGGGCCAAAGTGATTATTGAGCAGAGTTGGGGAAGTCCCAAAGTAACAAAA
      LeuLeuAlaAspAlaValAlaValAlaThrMetGlyProLysGlyArgThrValIleIleGluGlnSerTrpGlySerProLysValThrLys  75

226  GATGGTGTGACTGTTGCAAAGTCAATTGACTTAAAAGATCAATAAAGATAATACAAGAACATTGGAGCTAAACTGTTCAAGATGTTGCCAATAACACA
      AspGlyValThrValAlaLysSerIleAspLeuLysAspLysTyrLysAsnIleGlyAlaAlaLysValGlnAspValAlaAlaAsnAsnThr  105

316  AATGAAGGAGCTGGGGATGGCACTACCACTGTCTACTGGCACGCTCTATAGCCAAGGACTTCGAGAAGATTAGCAAGGTGCT
      AsnGluGluAlaGlyAspGlyThrThrThrAlaThrValLeuAlaArgSerIleAlaAlaLysGluGlyPheGluLysIleSerLysGlyAla  135

406  AATCCAGTGGAAATCAGGAGAGAGGTGTAGCTGTTGATGCTGTAATTGCTGAAACTAAAAGCAGTCTAAACCTGTGACCACCCT
      AsnProValGluIleArgArgGlyValMetLeuAlaValAspAlaValIleAlaGluLeuLysLysGlnSerLysProValThrThrPro  165

496  GAAGAAATTGCACAGGTTGCTACGATTTCTGCAAACGACAAAGAAATTGGCAATATCATCTCTGATGCAATGAAAAAGTTGGAAGA
      GluGluIleAlaGlnValAlaThrIleSerAlaAsnGlyAspLysGluIleGlyAsnIleIleSerAspAlaMetLysLysValGlyArg  195

586  AAGGGTGTCATCACAGTAAAGGATGAAAAAACACTGAATTGTGAAGGTGTTGAAGGTGCATGAAGTTTGATGCGAGGCTATATTTCT
      LysGlyValIleThrValLysAspGlyLysThrLeuAsnAspGluGluIleGluGlyMetLysPheAspArgGlyTyrIleSer  225

676  CCATACTTATTAATAACATCAAAAGGTCAGAAATGTGAATTCCAGGATGCCCTATGTTCTGTTGACTGAAAAAGAAATTTCTAGTATCCAG
      ProTyrPheIleAsnThrSerLysGlyGlnLysCysGluPheGlnAspAlaTyrValLeuLeuSerGluLysIleSerIleGln  255

766  TCCATTGTACCTGCTCTTGAAATTGCCAATGCTCAGCCTTTGGTCATAATGCTGAAGATGTTGATGAGAAGCTCTAAGTACA
      SerIleValProAlaLeuGluIleAlaAsnAlaHisArgLysProLeuValIleMetLeuLysAspValAlaValLysAlaProGlyPhe  285

856  CTCGTCTTGAATAGGCTAAACGTTGGTCTTCAGGTTCCAGGTTTGGTGACAATAGAAAGAACCAGCTTAAAGAT
      LeuValLeuAsnArgLeuLysValGlyLeuLysLysAlaProGlyPheGlyAspAsnArgLysAsnGlnLeuLysAspAsp  315
```

Fig. 3B

KIT FOR THE DIAGNOSIS OF INSULIN DEPENDENT DIABETES MELLITUS

CROSS-REFERENCE TO RELATED APPLICATION

The present application is a division of application Ser. No. 07/848,517, filed Mar. 9, 1992, now abandoned, which was a division of application Ser. No. 07/371,249, filed Jun. 26, 1989, now U.S. Pat. No. 5,114,844, which, in turn, was a continuation-in-part application of Ser. No. 07/322,864, filed Mar. 24, 1989, now abandoned, the entire contents of which are hereby incorporated by reference.

FIELD OF THE INVENTION

The present invention relates to a method for detecting the existence of, a tendency to develop, or the initiation of a process leading to insulin dependent diabetes mellitus (IDDM), and, more particularly, to such a method which detects the presence of a 65 KD heat shock protein (hsp65) or antibodies to this protein.

The present invention further relates to a method for the prevention of IDDM or the treatment of IDDM in its incipient stages by administering hsp65 in such a manner as to cause immunological tolerance therefor.

BACKGROUND OF THE INVENTION

Insulin dependent diabetes mellitus (IDDM) is caused by an autoimmune process which destroys the insulin-producing beta cells. Diabetes becomes clinically evident only after the vast majority of beta cells are irrevocably destroyed (perhaps 90%) and the life of the individual becomes dependent on an exogenous supply of insulin. In other words, at the time of clinical diagnosis, the autoimmune process has already done irreversible damage, most of it without noticeable symptoms.

Successful treatment of the autoimmune process responsible for the disease ideally should be initiated before the patient has overt symptoms of diabetes and requires insulin replacement for his or her own lost capability to produce insulin. Termination of the autoimmune process would result in cure of the disease and prevention of the need for exogenous insulin only if the disease process could be halted while the patient still possessed a sufficient number of beta cells to provide adequate amounts of endogenous insulin. Therefore, any form of therapy would be more effective if persons at risk could be identified while they were yet without overt symptoms of IDDM and before the patients require exogenous insulin. About 90% of new cases of IDDM occur outside of families with known cases. Therefore, assays suitable for mass screening are urgently needed to detect the subclinical disease process at a stage before it is irreversible.

Fortunately, there are a variety of animal models for IDDM, including BB rats and NOD mice (for example, see Rossini et al., *Ann. Rev. Immunol.*, 3:289–320, 1985). Many of the animals develop autoimmune IDDM spontaneously, and demonstrate many of the features of IDDM in humans.

Heat shock proteins (hsp's) are a family of proteins produced by cells exposed to elevated temperatures or other stresses. The hsp's include proteins of various molecular weights, including 20KD, 65–68KD, 70 KD, 90 KD, 110 KD, and others. The heat shock proteins are ubiquitous throughout nature; they are produced by bacteria, yeasts, plants, insects, and higher animals, including humans. The hsp protein molecules are highly conserved and show remarkable homology between all of these diverse creatures. Because of their extreme conservation over evolutionary time, heat shock proteins are thought to perform vital functions. They usually exhibit increased synthesis following exposure of cells to stressful stimuli including heat, certain metals, drugs, or amino acid analogues. Nevertheless, the special functions of these proteins so far are obscure.

For example, patients with systemic lupus erythematosus (SLE) were observed to have antibodies to a 90 KD heat shock protein (Minota et el., *J. Clin. Invest.*, 81:106–109, 1988). The function of these antibodies to hsp90 are not known.

Hsp65 was found to be involved in adjuvant arthritis in rats, cf. van Eden et al., *Nature*, 331:171–173, 1988. Adjuvant arthritis is an autoimmune arthritis triggered by immunizing certain strains of rats to *Mycobacterium tuberculosis* (MT) organisms. It was found that the disease could be transferred to immunologically naive, irradiated rats by a clone of T-lymphocytes reactive to a 9 amino acid peptide sequence (180–188) of the hsp65 of MT. Thus, adjuvant arthritis appeared to be an autoimmune disease produced by anti-hsp65 T-lymphocytes. The autoimmune attack against the Joints was attributed to partial sequence homology between the 180–185 hsp65 peptide and a segment of the link protein of the cartilage proteoglycan (cf. Cohen, *Scientific American*, 258:52–60, 1988). It was also found that T-lymphocytes from the synovial fluids of patients with rheumatoid arthritis responded to the hsp65 of MT (cf. Res et al., *Lancet*, II:478–480, (1988).

Administration of hsp65 to rats before induction of adjuvant arthritis was found to prevent the later development of arthritis. Thus, the presence of an immune response to hsp65 was associated with arthritis in both rats and humans, and administration of hsp65 could lead to resistance to arthritis.

European patent application 262,710 discloses polypeptides useful for alleviation, treatment, and diagnosis of autoimmune arthritis and similar autoimmune diseases.

The complete primary structure, including nucleotide and deduced amino acid sequence of the human P1 protein has recently been published in Jindal, S. et al, "Primary Structure of a Human Mitochondrial Protein Homologous to the Bacterial and Plant Chaperonins and to the 65-Kilodalton Mycobacterial Antigen," *Molecular and Cellular Biology*, 9, 5, 2279–2283, 1989. This protein, disclosed as having a molecular weight of about 63 kDa, is the human heat shock protein referred to herein as the hHSP65 protein. The entire contents of this publication are hereby incorporated herein by reference.

SUMMARY OF THE INVENTION

It is an object of the present invention to provide a method of early diagnosis of insulin dependent diabetes mellitus (IDDM).

It is a further object of the present invention to provide kits for use in the early diagnosis of IDDM.

It is another object of the present invention to provide a method for the prevention of IDDM.

It is yet another object of the present invention to provide a method for the treatment of IDDM in its incipient stages.

It is still a further object of the present invention to provide a tolerogenic composition for the prevention or treatment of IDDM.

According to the discovery of the present invention, in the course of developing IDDM, animals express hsp65 molecules which find their way into the blood and urine of the animals. They also express antibodies to the hsp65 molecule. Thus, the presence of hsp65 or antibodies to hsp65 in blood or urine serves as an assay for the detection of the IDDM process before the destruction of beta cells is completed and the individual is doomed to life-long diabetes.

The presence or incipience of IDDM in a patient can be diagnosed by testing for the presence of hsp65 or antibodies to hsp65.

The present invention also relates to means for performing such assays, as well as kits for performing such assays. The detection of incipient diabetes then permits a patient to begin measures aimed at terminating the autoimmune process. For example, the administration of hsp65 is effective in inducing resistance to the autoimmune process involved in IDDM.

The present invention further relates to means for preventing or treating IDDM. It has been discovered that immunization to hsp65 in an appropriate adjuvant can induce IDDM. However, vaccination with hsp65 without an effective adjuvant, and preferably with a tolerogenic carrier, can produce a specific tolerance to the antigen. This effectively creates a resistance to the autoimmune process of IDDM. If the patient is shown to already be in the preclinical incipient stages of IDDM, injection with such an antigen can create a tolerance for this antigen and thus arrest the autoimmune process before significant, permanent damage is done.

BRIEF DESCRIPTION OF THE DRAWINGS

The present invention will be better understood from the following brief description of the drawings and the subsequent detailed description of the preferred embodiments.

FIG. 3A-B shows the nucleotide and deduced amino acid sequences of the human P1 protein, which is an hHSP65. Numbers on the left refer to the nucleotide sequence relative to coordinate 1 at the beginning of the putative initiation codon. The amino acid sequence is numbered starting with 1 at the same point. The 5' extension of this reading frame is shown in one-letter code. The position of the internal EcoRI site (nt 712), which marks the beginning of the λ22a sequence, is indicated. The polyadenylation signal 15 nt from the A tail at the 3' end is underlined. The putative mitochondrial targeting sequence at the N-terminal end and a keratinlike amino acid sequence at the C-terminal end containing repeats of Gly-Gly-Met are boxed. Positively charged amino acids in the leader sequence are identified (+).

DETAILED DESCRIPTION OF PREFERRED EMBODIMENTS

Figure 3B:
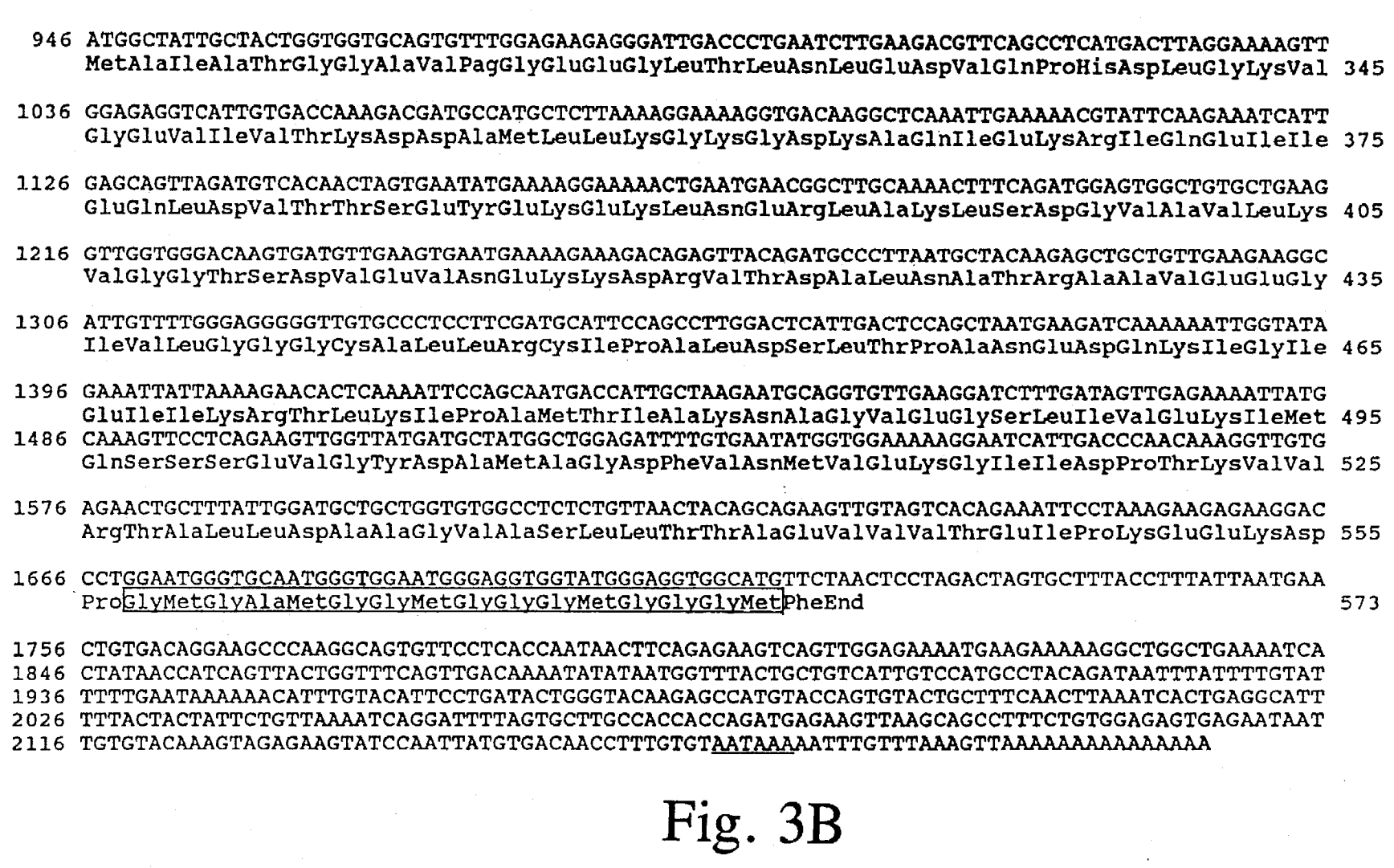
Figure 1:
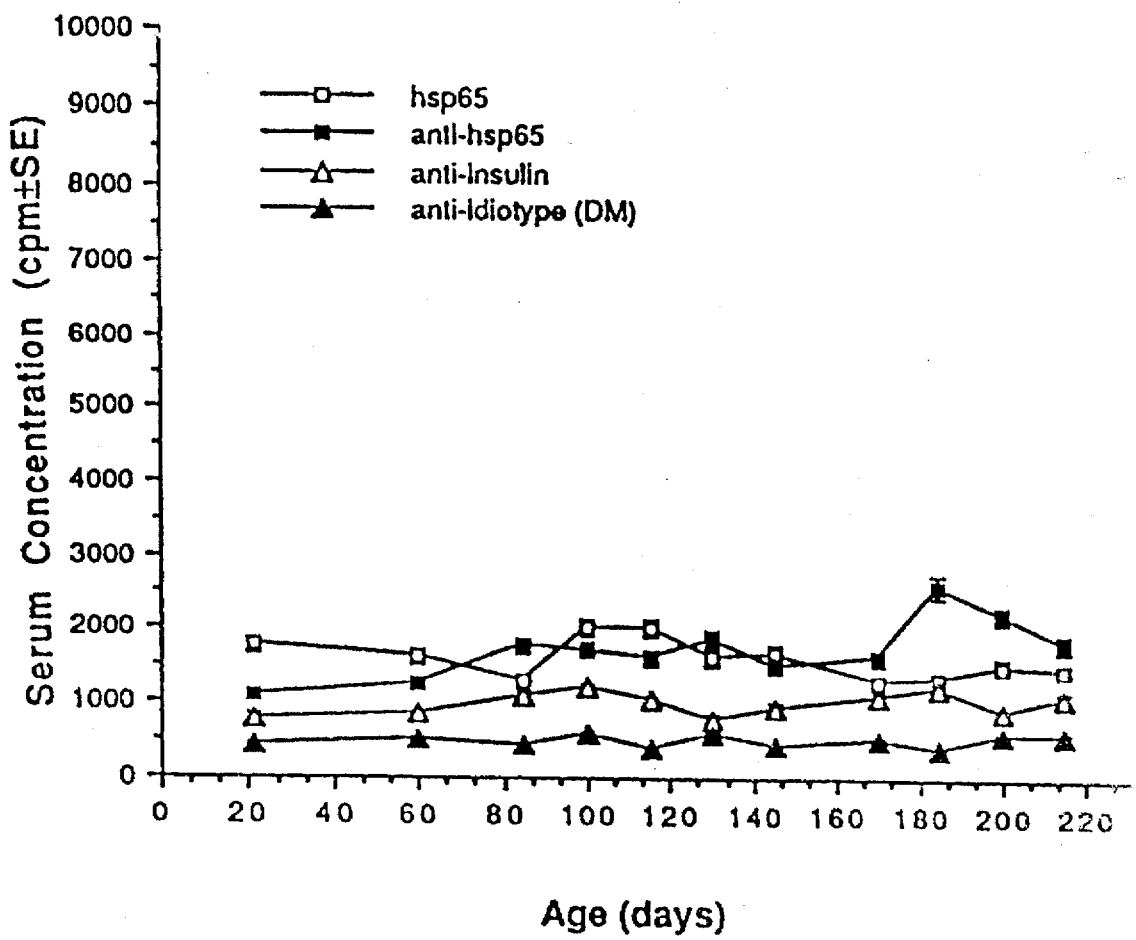
FIG. 1 shows the amounts of hsp65, anti-hsp65, anti-insulin antibody, and anti-idiotypic antibody in the serum of NOD mice that did not develop IDDM.

The particular protein produced by the human body during development of IDDM, which serves as a diagnostic marker in accordance with the present invention for the incipient outbreak of IDDM, is the human heat shock protein having a size of about 65 KD. The nucleotide and deduced amino acid sequence of this protein are set forth in FIG. 3A-B. This protein will hereinafter be referred to as hHSP65. It has been discovered, however, that other proteins may also be present which cross-react to the same antibodies which bind the 65 KD protein. For example, in mice and rats, 47 KD, 30 KD and 25 KD molecules were found which also cross-react with a monoclonal antibody specific to the hsp65 molecule of M. tuberculosis. A 47 KD molecule has also been discovered in rat fibroblasts which is cross-reactive with such an antibody. In view of the cross-species preservation of heat shock protein, it is fully expected that these will also be present in humans. Accordingly, for the purpose of the present specification and claims, the term "hHSP65" is intended to comprehend not only the 65 KD human heat shock protein, but also any other related molecule found in the human serum which cross-reacts with polyclonal antibodies raised against a 65 KD heat shock protein of any species. This definition is specifically intended to include, although it is not limited to, the 65 KD, 30 KD, 25 KD and 47 KD proteins which have already been discovered and are discussed herein..

Because of the structural similarities of heat shock proteins throughout nature, the presence of hHSP65 can be detected by polyclonal or monoclonal antibodies specifically raised against the heat shock protein of any organism. For example, the heat shock protein of M. tuberculosis (MT) can be readily produced in high quantity by genetic engineering techniques. This protein can be used to raise antibodies in rabbits or mice. The polyclonal rabbit anti-MT-hsp65 antibodies can be used in accordance with the present invention to assay for the presence of hHSP65. Similarly, monoclonal antibodies obtained from the spleens of mice immunized against MT hsp65 can be selected which react with MT hsp65. Such monoclonal antibodies will also cross-react with hHSP65.

Those of ordinary skill in the art will know of many ways to raise antibodies reactive or cross-reactive to hHSP65, once one is aware of the diagnostic capabilities of hHSP65. Any of such antibodies may be used in accordance with the present invention. Due to the structural similarities, the hsp of any organism can be used as an immunization agent and the antibodies can be raised in any organism. Any specific monoclonal antibodies used in the examples of the present specification are for the purpose of exemplification only. There is no reason to believe that any one such monoclonal antibody specifically raised for its property of specifically reacting with a given antigen, would be better than any other for the purpose of the present invention.

As indicated above, not only can the hHSP65 protein be used as the diagnostic marker, but antibodies against hHSP65 can also be used as such. Antibodies which spontaneously form when hHSP65 is released in the human patient can be assayed. A positive assay for the presence of such antibodies will serve as an indication of impending IDDM to the same extent as an assay for the hHSP65 proteins themselves will serve this purpose. The anti-hHSP65 antibodies may be assayed for by looking for reaction with any hsp65 protein. Thus, the MT hsp65 protein will cross-react with anti-hHSP65 antibodies. Of course, the preferred protein for use in assaying for the presence of anti-hHSP65 antibodies is the hHSP65 protein. However, those of ordinary skill in the art can readily empirically determine, without undue experimentation, whether any given protein or protein fragment will cross-react with anti-hHSP65 antibodies. Simple in vitro tests can be used to determine if any such protein or other molecule will immunoreact with anti-hHSP65 antibodies.. If it does, then it can be used in the method of the present invention and it is intended to be comprehended by the present invention.

The following examples show specific embodiments of the present invention and experiments relating to the present invention. These are intended as examples only and are presented in a non-limitative manner.

EXAMPLE 1: Production of the MT hsp65 Molecule

The hsp molecule of *Mycobacterium tuberculosis* was transfected into *E. coli* by standard procedures and purified as described by van Eden et al, *Nature,* 331:171–173, 1988. Such genetically engineered *E. coli* cells will produce substantial quantities of MT hsp65. Because of the close homology between hsp's of various sources, hsp65 of mammalian or human origin is also effective when produced by genetic engineering or isolation from cells.

EXAMPLE 2: Production of Antibodies to MT hsp65

Rabbits of a standard laboratory strain (New Zealand White) were inoculated subcutaneously in the back with 100 micrograms of MT hsp65 produced in accordance with Example 1, in 0.5 ml saline emulsified in 0.5 ml mineral oil (incomplete adjuvant). One month later the rabbits were boosted with 100 micrograms of MT hsp65 in 1.0 ml saline, and two weeks later the rabbits were bled and the serum collected. The rabbits were boosted in a similar manner after two months and bled again. The sera antibodies were used to detect hsp65 in the blood and urine of test animals and humans.

EXAMPLE 3: Assay of hsp65

A standard solid phase radioimmunoassay is used to detect the presence of hsp65 molecule. Flexible PVC microtiter plates are coated with 100 µl test serum or urine for 18 hours at 4° C. and washed with phosphate buffered saline (PBS). Control rabbit serum or anti-hsp65 serum (produced in accordance with Example 2) is then diluted 1:100 in PBS+0.1% bovine serum albumin (BSA), and 50 µl is added to each well and incubated for 2–3 hours at 37° C. The wells are then washed three times in PBS. $^{125}$I-goat anti-rabbit Ig, 100,000 cpm/well, is added and the wells are maintained for two hours at 37° C. The plates are then washed four times in PBS and dried, and the wells are counted in a gamma counter. Values obtained with anti-hsp65 serum 2 S.D. above the mean cpm obtained with normal rabbit serum are considered as positive for the presence of hsp65.

EXAMPLE 4: Assay of Anti-hsp65 Antibodies

Antibodies to hsp65 are detected in a similar fashion except that the antigen bound to the plates is not test serum or urine, but purified MT hsp65 produced in accordance with Example 1, 5 µm/well. The serum to be tested for anti-hsp65 antibodies is diluted 1:50. Urine is used undiluted. The serum or urine is added to the wells containing hsp65 and the presence of antibodies binding to hsp65 is detected using radiolabelled goat anti-mouse Ig for mouse specimens and goat anti-human Ig for human specimens. The remainder of the assay is done as described in Example 3. Positive results are defined as cpm greater than 2 S.D. above the mean cpm obtained using control sera from healthy mice, rats, or humans.

EXAMPLE 5: hsp65 Molecules and Anti-hsp65 Antibodies Detect Development of IDDM Before Its Onset NOD Mice Fourteen female NOD mice were bled beginning on day 21 of life at regular intervals for about 200 days and scored for the development of IDDM. The sera were tested for hsp65, anti-hsp65, anti-insulin antibodies, and anti-idiotypic antibodies to DM idiotype.

The hsp65 was tested using the assay of Example 3. The presence of anti-hsp65 antibodies was assayed according to the procedure of Example 4. Anti-insulin antibodies are idiotypic antibodies which recognize the receptor binding sites of insulin, sometimes designated DM-idiotypic antibodies. Anti-idiotypic antibodies are antibodies against DM-idiotypic antibodies, sometimes designated anti-DM-idiotypic antibodies. In U.S. application Ser. No. 07/295,401, owned by the present assignee, it is disclosed that the presence of DM-idiotypic antibodies or anti-DM-idiotypic antibodies in the serum or urine of a patient is a positive indication of incipient or active IDDM. Such antibodies are not present in the serum or urine of healthy patients. The procedures used to assay for the presence of anti-insulin antibodies and anti-idiotypic antibodies are as set forth in said Ser. No. 07/295,401, the entire contents of which are hereby incorporated herein by reference.

Figure 2:
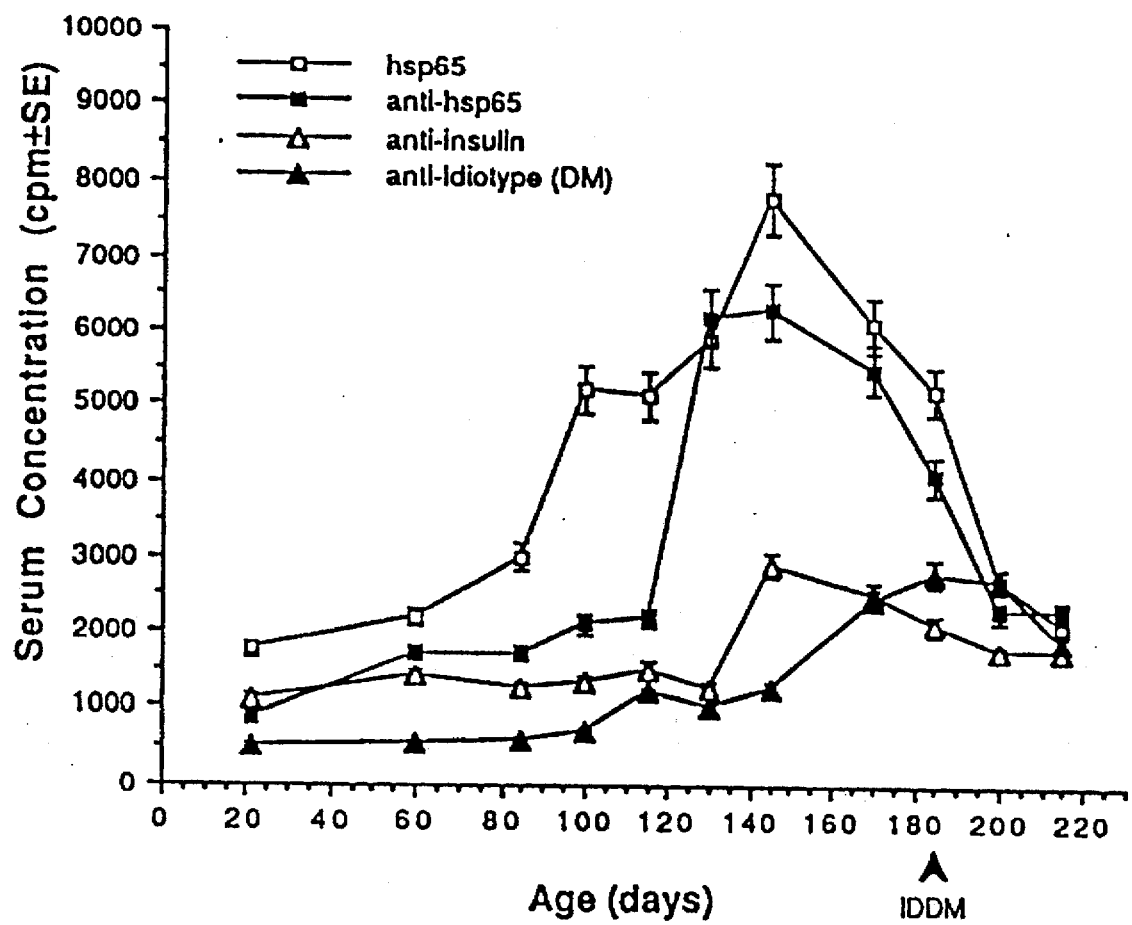
FIG. 2 is a graph showing that marked increases in hsp65 and anti-hsp65 precede the development of overt IDDM in NOD mice that did develop the disease. Anti-insulin and idiotypic (DM) antibodies preceded IDDM by a lesser extent.

Ten of the NOD mice developed IDDM and four remained free of IDDM. FIG. 1 shows the results of testing the sera of one mouse that did not develop IDDM, and FIG. 2 shows the results of testing the sera of one of the mice that did develop IDDM. It can be seen that compared to the IDDM free mouse, the mouse that did develop IDDM on day 185 of life developed a markedly elevated concentration of hsp65 beginning on day 85. The hsp65 concentration decreased after IDDM actually appeared. Anti-hsp65 antibodies appeared several weeks after the appearance of hsp65. Anti-insulin and anti-idiotypic (DM) antibodies appeared much later. Thus, elevation of hsp65 and anti-hsp65 preceded clinical IDDM and served as early signs of the subclinical disease process.

Table 1 shows the cumulative data obtained from the fourteen individual mice.

TABLE 1

Serum Assay of Impending IDDM in NOD Mice

| Mouse | Day of IDDM onset | Days Positive Test Preceded IDDM Onset | | | |
|---|---|---|---|---|---|
| | | hsp65 | anti-hsp65 | anti-insulin | anti-idiotype |
| 1 | none | 0 | 0 | 0 | 0 |
| 2 | none | 0 | 0 | 0 | 0 |
| 3 | none | 0 | 0 | 0 | 0 |
| 4 | none | 0 | 0 | 0 | 0 |
| 5 | 185 | 90 | 45 | 45 | 30 |
| 6 | 185 | 100 | 50 | 45 | 20 |
| 7 | 170 | 90 | 60 | 60 | 30 |
| 8 | 170 | 100 | 50 | 30 | 20 |
| 9 | 145 | 60 | 60 | 25 | 15 |
| 10 | 145 | 70 | 30 | 15 | 15 |
| 11 | 145 | 60 | 40 | 20 | 20 |
| 12 | 130 | 50 | 20 | 0 | 0 |
| 13 | 115 | 55 | 55 | 20 | 20 |
| 14 | 115 | 50 | 30 | 30 | 20 |
| Mean | 150.5 | 72.5 | 44 | 29 | 19 |
| SE | 8.28 | 6.47 | 4.33 | 5.47 | 2.67 |
| Median | 145 | 65 | 47.5 | 27.5 | 20 |

The mean age of IDDM onset was 150.5 days in the mice developing disease. The mean hsp65 serum test was positive 72.5 days before IDDM and the mean anti-hsp65 test was positive 44 days before IDDM. The anti-insulin and anti-idiotypic antibody tests were positive only 29 and 19 days before IDDM on the average. The tests were not significantly positive in mice escaping IDDM. Therefore, hsp65 and anti-hsp65 are relatively early indicators of eventual development of IDDM.

Urine was tested for the presence of hsp65 in the NOD mice at about 100 days of age. Table 2 shows that the urine of the mice tested positive in those mice that did develop IDDM.

TABLE 2

Urine Assay of Impending IDDM in NOD Mice

| IDDM | Urines positive for hsp65 |
| --- | --- |
| Yes | 10/10 |
| No | 0/4 |

BB Rats

Table 3 shows that BB rats that did not develop IDDM did not manifest hsp65 or anti-hsp65 in the serum or urine. Rats that did develop IDDM (on days 90–100) were positive when tested 10 to 20 days before the outbreak of IDDM. The assays were conducted as disclosed in Examples 3 and 4.

TABLE 3

Assays of hsp65 and Anti-hsp65 Associated with Development of IDDM in BB Rats

| Development of IDDM | Serum | | Urine | |
| --- | --- | --- | --- | --- |
| | hsp65 | anti-hsp65 | hsp65 | anti-hsp65 |
| Yes | 10/10 | 5/5 | 4/5 | 3/5 |
| No | 0/5 | 0/5 | 0/5 | 0/5 |

Human IDDM Patients

Sera were available from five patients at various times before they developed IDDM. The sera were obtained from these persons ½ to 2 years before the onset of IDDM because they were first degree relatives of known IDDM patients and were thought to be at risk of developing IDDM themselves.

In addition to those persons, sera and urines of four newly diagnosed IDDM patients were studied for hsp65. Control sera and urines were obtained from 10 patients with active multiple sclerosis and 35 children seen at a general hospital for a variety of problems not related to IDDM. The results are shown in Table 4. The assays were conducted in accordance with the procedures of Examples 3 and 4.

TABLE 4 hHSP65 and anti-hHSP65 in human IDDM patients

| Humans | Serum | | Urine | |
| --- | --- | --- | --- | --- |
| | hHSP65 | anti-hHSP65 | hHSP65 | anti-hHSP65 |
| Pre-IDDM | 4/5 | 4/5 | N.D. | N.D. |
| New IDDM | 2/4 | 2/4 | 2/4 | 2/4 |
| Multiple Sclerosis | 0/10 | 0/10 | N.D. | N.D. |
| Hospitalized Children (no IDDM) | 0/35 | 0/35 | N.D. | N.D. |
| Healthy adults | 0/10 | 0/10 | 0/10 | 0/10 |

It can be seen from the above table that four out of five of the pre-IDDM patents and two out of four of the IDDM patients were positive in the hHSP65 and anti-hHSP65 assays. None of the controls was positive. Thus, anti-hsp65 raised in rabbits against hsp65 of MT can detect hHSP65 in human serum and urine in association with the development of IDDM. Moreover, hsp65 of MT could detect human antibodies. As discussed above, antibodies made to hsp65 of human or other origin can also be used in these assays, as well as hsp65 obtained from human or other sources. This is possible because of the high degree of conservation of hsp's throughout biological evolution.

That all of the pre-IDDM and new IDDM patients were not positive is explained by the fact that the concentrations of hHSP65 and anti-hHSP65 tend to decrease at or around the actual time of IDDM onset, as shown in FIG. 2. Thus, the negative patients may have lost their positivity when they were tested close to the onset of IDDM.

From the above, it is apparent that human patients will be positive for hHSP65 or anti-hHSP65 at some time early before the onset of IDDM. Assays for hHSP65 or anti-hHSP65 are therefore useful in screening populations for those that may be in the process of developing IDDM.

The hHSP65 appearing in the blood or urine of individuals developing IDDM could come from several sources. The sources may be hHSP65 expressed normally by healthy beta cells and released when the beta cells undergo viral infection or toxic insult as a prelude to immunological destruction, or it may be released from the beta cells by the stress of immunological destruction. The hHSP65 might also be expressed by the cells of the immune system during their prolonged activity against the beta cells. Although the sources of hHSP65 in the system are not at this time conclusively known, it has been determined that once the hHSP65 is released, the individual is stimulated to make antibodies to the hHSP65 molecule.

Antibodies to an undefined molecule of 64,000 molecular weight have been described in some newly diagnosed IDDM patients by Baekeskov et al. in *Nature*, 298: 167–168, 1982. However, it is not known whether the 64 KD antigen is an hsp. Moreover, the 64 KD antigen is not known to appear in blood or urine before the onset of IDDM. In contrast to this undefined 64KD beta cell antigen, hsp65 is a defined protein whose amino acid sequence is known (Thole et al, *Infection and Immunity*, 55:1466–1475, 1987). Similarly, the amino acid sequence of hHSP65 is shown and set forth in FIG. 3A–B.

EXAMPLE 6: Study of Male Mice of Strain C57BL/Ksj

C57BL/KsJ mice develop IDDM approximately two weeks after receiving five consecutive daily inoculations of the beta cell toxin streptozotocin at doses of 40 mg/kg per day.

In the experiments described herein, groups of ten male C57BL/Ksj mice, aged 3 months, were or were not subjected to low-dose streptozotocin injections (40 mg/kg daily×5) to induce IDDM (appearing at day 14) and were investigated for the development of IDDM, as measured by blood glucose higher than 250 mg %, and for the appearance of hsp65 and anti-hsp65 antibodies in the blood. As shown in Table 5, the hsp65 appeared by day 10 (before clinical manifestation of IDDM), followed by anti-hsp65.

TABLE 5

Low-dose streptozotocin model of IDDM in C57Bl/ksj mice:
Induction of hsp65 and anti-hsp65

| Appearance of | Streptozotocin | IDDM Cumulative Incidence on Days | | | |
|---|---|---|---|---|---|
| | | 0 | 5 | 10 | 25 |
| IDDM | Yes | 0 | 0 | 0 | 100 |
| | No | 0 | 0 | 0 | 0 |
| hsp65 | Yes | 0 | 0 | 90 | 100 |
| | No | 0 | 0 | 0 | 0 |
| anti-hsp65 | Yes | 0 | 0 | 0 | 90 |
| | No | 0 | 0 | 0 | 0 |

EXAMPLE 7: Multiple Murine Molecules are Cross-Reactive with hsp65 of Mycobacteria To identify the mammalian molecules recognized by antibodies to mycobacterial hsp65, the rabbit anti-hsp65 antiserum described above was tested, as was a monoclonal antibody designated as TB78. This antibody was developed and supplied by Dr. J. Ivanyi, of the MRC Tuberculosis Unit, Hammersmith Hospital, London. This antibody is specific for the hsp65 molecule of *M. tuberculosis*. Three types of preparations were assayed for their binding of these antibodies: Cloned hsp65 of M. tuberculosis; the sera of NOD mice developing IDDM and healthy controls; and lysates of rat fibroblasts treated with heat shock and control fibroblast lysates.

Hsp65 was prepared as described in Example 1. Rat embryonic-fibroblasts were cultured using standard procedures. To induce heat shock proteins, cultures of fibroblasts were incubated at 42.5° C. for two hours and then for ½ hour at 37° C. The heat shocked fibroblasts and control fibroblasts were cultured at 37° C., and about $5 \times 10^6$ cells each were then lysed using a lysis buffer composed of 0.1% SDS and 1% Triton together with protease inhibitors. The protein concentration was adjusted by Bradford determination to 2 mg/ml. The material was run in 10% polyacrylamide gel, 100 micrograms per lane, for standard electrophoresis, under reducing conditions (2% 2-mercaptoethanol). Mouse sera from healthy control mice and from NOD mice developing IDDM were diluted to a concentration of 2 mg/ml. Each of these serum preparations was separated by polyacrylamide gel electrophoresis as above. The separated proteins were then transferred overnight to nitrocellulose paper by standard procedures. The papers were then incubated for one hour at room temperature with 1% hemoglobin (for blocking) and then with either normal rabbit serum or anti-hsp65 at a dilution of 1:100, or with TB 78 or a control monoclonal antibody at dilutions of 1:100 for two hours at room temperature. Binding of the antibodies to any of the separated bands was detected by incubation with $^{125}$I-radiolabelled goat anti-rabbit Ig or goat anti-mouse Ig, washed and developed by autoradiography. Molecular weight standards were included.

It was found that several bands were detected by the anti-hsp65 antibodies. Mycobacterial hsp65 was detected by both the rabbit antiserum and monoclonal TB68. The antibodies also recognized a 65 KD band in the murine fibroblasts that was expressed in an augmented fashion after heat shock. In the heated fibroblast lysates there were also positive bands at 30 KD and 47 KD. An additional band at about 25 KD was detected in the sera from the NOD mice developing IDDM. Therefore, mammalian molecules of 65 KD, 47 KD, 30 KD and 25 KD are cross-reactive with mycobacterial hsp65.

EXAMPLE 8: Hsp65 is Expressed in the Islets of the Pancreas

Because the development of IDDM is accompanied by augmented expression of hsp65 in the blood and urine, it was thought that the beta cells in the islets might be the source of the hsp65. In order to test this theory, rabbit anti-hsp65 was tested to see if it would bind to islet cells.

A standard procedure was used to prepare frozen sections of rat pancreas, 6–8 microns thick. The sections were overlaid with normal rabbit serum or anti-hsp65 anti-serum (absorbed with liver powder to remove non-specific antibodies) diluted 1:50 and incubated for 30 minutes at room temperature, thoroughly washed with PBS, and then incubated for 5 minutes with 5% normal goat serum before incubation with fluorescein labelled goat anti-rabbit Ig for 30 minutes at room temperature, washed with PBS and examined using a fluorescence microscope. The islets were brightly stained by the anti-hsp65 antiserum, but not by the control rabbit serum. Therefore, islets express hsp65.

EXAMPLE 9: Immunization to hsp Induces IDDM

Since it was found that islet cells express hsp65, it was postulated that an anti-hsp immune response would damage beta cells and thereby induce IDDM. Male C57BL/KsJ mice, 8 weeks old, or female NOD mice, 4.5 weeks old, were immunized by intraperitoneal injection with 50 µg of hsp65 and tested as to whether they might develop IDDM, as evidenced by blood glucose greater than 250 mg %. At 4.5 weeks of age, the NOD mice were at least three months before spontaneous IDDM. The C57BL/Ksj mice do not develop spontaneous IDDM. The hsp65 was administered emulsified in oil or in PBS. Bovine serum albumin (BSA) emulsified in oil was used as a control. The results are shown in Table 6. It was found that hsp65 in oil, but not in PBS, induced IDDM. Therefore, an immune response to hsp65 can trigger IDDM, probably because the beta cells express an antigen cross-reactive with hsp65.

TABLE 6

| mice | antigen | adjuvant | Incidence of IDDM 3 weeks later |
|---|---|---|---|
| NOD | hsp65 | oil | 7/10 |
| | hsp65 | PBS | 0/10 |
| | BSA | oil | 0/20 |
| C57BL/ksj | hsp65 | oil | 6/7 |
| | hsp65 | PBS | 0/9 |
| | none | none | 0/15 |

In an additional experiment, strains of normal mice which do not develop IDDM spontaneously, as do NOD mice, or even after low dose streptozotocin, as do C57BL/ksJ mice, were inoculated intraperitoneally with 50 µg of antigen, either hsp65 or bovine serum antigen (BSA) emulsified in incomplete Freund's adjuvant (oil). The mice were bled in the morning 19 days later and blood glucose was measured. IDDM was diagnosed by a concentration of blood glucose greater than 200 mg%. The results are shown in Table 7. It can be seen that immunization with hsp65 can induce IDDM even in some apparently normal strains of mice, particularly when administered in an appropriate dosage. This supports the conclusion that hsp65 or molecules immunologically cross-reactive with hsp65, are target antigens in IDDM.

TABLE 7

Immunization to hsp65 Induces IDDM in Non-Diabetic Strains of Mice

| Mouse Strain | Blood Glucose (mg %) antigens | | IDDM Incidence antigens | |
|---|---|---|---|---|
| | hsp65 | BSA | hsp65 | BSA |
| C3H.eB/Fej | 270 ± 41 | 96 ± 32 | 5/5 | 0/5 |
| C57BL/6j | 298 ± 52 | 122 ± 26 | 5/5 | 0/5 |
| DBA/2 | 146 ± 33 | 126 ± 21 | 0/5 | 0/5 |
| SJL/j | 162 ± 27 | 139 ± 26 | 0/5 | 0/5 |

EXAMPLE 10: hsp65 Can Induce Resistance to Induction of IDDM

It is well established that antigen administered without an effective adjuvant, or with a tolerogenic carrier, can induce immunological non-responsiveness, i.e., specific tolerance to the antigen. Therefore, mice that had been injected with hsp65 in PBS were tested to determine if these mice had acquired resistance to IDDM induced by hsp65 in oil. One month after receiving hsp65 in PBS, C57BL/Ksj mice were challenged with hsp65 in oil, and none of these mice developed IDDM as measured by blood glucose greater than 250 mg % three weeks later. In contrast, 8 of 10 control mice that had not received hsp65 in PBS developed IDDM after receiving hsp65 in oil.

In another experiment, hsp65 was given to 30 day old female NOD mice in PBS, intraperitoneally, 15 days before challenge with 50 μg hsp65 in oil to induce IDDM. The presence of IDDM was measured by blood glucose concentration of greater than 200 mg% 35 days after challenge. The presence of IDDM was again measured when the mice were 5 months of age. At this age it is known that 50% of all untreated female NOD mice have detectable IDDM. The results are shown in Table 8.

TABLE 8

Use of hsp65 to Vaccinate against IDDM

| hsp65 in PBS (μg) | Incidence of IDOM | |
|---|---|---|
| | 35 days after challenge | 5 months old |
| 0 | 7/8 | |
| 1 | 0/8 | 0/8 |
| 5 | 0/8 | 0/8 |
| 50 | 0/8 | 0/8 |

Thus, it can be seen that hsp65 can be used to induce tolerance to a diabetogenic immune process. Not only is this tolerance effective with respect to an immunogenic attack of hsp65, but it remains effective as a treatment against the natural development of spontaneous IDDM in NOD mice.

EXAMPLE 11: Treatment of Incipient IDDM Using hHSP65

As shown in Example 10, hsp65 can be used to induce resistance to the autoimmune process of IDDM. This appears to be caused by a mechanism of immunological tolerance to the hHSP65 of the beta cells through exposure to exogenous hsp65. Thus, hsp65 can be useful in treating IDDM before the disease becomes clinically evident and the autoimmune process can be arrested before significant, permanent damage is done. The results of the experiment summarized in Table 8 to the effect that the natural development of spontaneous IDDM in NOD mice can be arrested is significant evidence that hsp65, and particularly hHSP65, can be used therapeutically. The autoimmune process begins very early in NOD mice. At the age of one month insulitis can already be detected. IDDM becomes clinically evident at 5 months in 50% of the female mice of this strain. Administration of hsp65 in 30 day old mice stops this natural development. This establishes that treatment can be effective even after autoimmunity to the islets has already begun.

The hsp65 can be used as a therapeutic composition which will be effective against continued development of IDDM by creating tolerance to hHSP65 and thus stopping the self-destruction of the beta cells. The active principle for use in such treatment of incipient IDDM can be any material which is immunologically cross-reactive with hHSP65, i.e., it either cross-reacts with polyclonal antibodies raised against hHSP65 or it raises antibodies which cross-react with hHSP65. Such material, be it a peptide, protein, carbohydrate or other substance, if administered in a tolerogenic manner, will serve to induce tolerance to hHSP65 by virtue of this cross-reactivity. If the substance is an hsp65 protein, it can come from any species. The substance need not be an entire protein in order to be immunologically cross-reactive with hHSP65. It could be a fragment of the protein which retains the antigenic activity of the protein itself. Indeed, it may even be the 9 amino acid peptide sequence (180–188) of the hsp65 of MT identified as the immunologically active portion of hsp65 insofar as adjuvant arthritis is concerned in Van Eden et al, supra, the entire contents of which are hereby incorporated by reference. Routine experimentation will determine whether any given substance is cross-reactive with hHSP65. If the substance cross-reacts with a polyclonal antibody raised against hHSP65 or if it raises antibodies which are cross-reactive with hHSP65, then it is intended to be within the scope of the present invention insofar as therapy of incipient IDDM is concerned. Additional verification of the capability of such a substance to be operable in human therapy would be by means of testing for induction of tolerance in the mouse test described in Example 10. Such experimentation would be routine and would not involve undue experimentation.

The preferred compound for treatment of human IDDM is hHSP65. The amino acid sequence of a human heat shock protein has now been elucidated and is set forth in FIG. 3A–B. This protein may be used for this purpose.

Besides the hsp65 protein discussed herein, salts, functional derivatives, precursors and active fractions thereof having the ability to immunologically cross-react with hHSP65 may also be used. Sequences such as those of FIG. 3A–B or those disclosed in Van Eden et al, supra, in which one or more amino acids are deleted or replaced with other amino acids, are intended to be encompassed by the present invention as long as they have the ability to immunologically cross-react with hHSP65.

As used herein the term "salts" refers to both salts of carboxyl groups and to acid addition salts of amino groups of the protein molecule. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid.

"Functional derivatives" as used herein covers derivatives which may be prepared from the functional groups which occur as side chains on the residues or the N- or C- terminal groups, by means known in the art, and are included in the invention as long as they remain pharmaceutically acceptable, i.e., they do not destroy the activity of the protein and do not confer toxic properties on compositions containing it.

These derivatives may, for example, include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

"Precursors" are compounds formed prior to, and converted into, hsp65 in the animal or human body.

As "active fractions" of the substantially purified protein, the present invention covers any fragment or precursors of the polypeptide chain of an hsp65 protein molecule alone or together with associated molecules or residues linked thereto, e.g., sugar or phosphate residues, or aggregates of the protein molecule or the sugar residues by themselves, provided said fraction has the ability to immunologically cross-react with hHSP65.

It is critical that the active principle described above be administered in a manner which will induce tolerance rather than inducing an immunogenic response. Thus, it should not be administered in oil or any other immunogenic adjuvant. A preferred way of administering the active principle such that it will induce tolerance is to administer it with a carrier that favors induction of tolerance to the antigen when the antigen-carrier conjugate is administered. Such carriers are known as tolerogenic carriers. Examples of known tolerogenic carriers are polymers of D-amino acids, polyethylene glycol, polymers of sugar molecules, self-IgG molecules, self-spleen cells, and fatty acid molecules. An antigen may also be administered in a monomeric highly soluble form to induce tolerance. Another known method of inducing tolerance to an antigen is to administer it orally, even without any carrier specifically chosen for its tolerogenic characteristics. Particular manners of administering an antigen so as to induce tolerance are known to those of ordinary skill in the art and any such manner may be used in accordance with the present invention. Such techniques are not, per se, part of the present invention.

Such a tolerogenic composition may be administered as a vaccine for the prevention of the development of IDDM, for example in family members of IDDM patients who may be genetically at risk for the development of IDDM. Preferably, however, the composition is used to stop the continued development of IDDM in persons having detectable hHSP65 in the blood or urine but preferably before they have developed an immune response to the hHSP65. Induction of tolerance will prevent that immune response and therefore prevent the damage (IDDM) caused by an uncontrolled anti-hHSP65 response. However, it is not too late to use the composition of the present invention as treatment even after the appearance of anti-hHSP65 antibodies. The experiment the results of which are shown in Table 8 establishes that the present invention can serve to stop the immune response even after autoimmunity to the islets has already begun. As the autoimmune process may take years in humans, even down-regulation of the response would be beneficial.

The composition in accordance with the present invention may be administered orally or parenterally, such as subcutaneously, intramuscularly, intravenously, intranasally or intrarectally. The pharmaceutical tolerogenic compositions may be prepared in a manner known in the art.

As shown from the above experiments, islet cells and heat shocked fibroblasts release molecules cross-reactive with mycobacterial hsp65. The fact that immunization of mycobacterial hsp65 can cause IDDM indicates that an immune attack against antigens cross-reactive with mycobacterial hsp65 damages beta cells. Such an immune response could occur as a primary event following accidental immunization to a cross-reactive hHSP65 or an invading microbe. The release of hHSP65 could also arise subsequent to beta cell damage inflicted by a virus or toxins. Thus, it can be understood why the appearance of the hsp65 positive molecules in the blood and urine is an early sign of developing IDDM, because the molecules are released from the beta cells as damage proceeds. Similarly, anti-hHSP65 antibodies are a reliable sign of impending IDDM because an immune response to hHSP65 can itself cause IDDM.

Whether the antibodies to hHSP65 are originally raised following accidental immunization or following release of hHSP65 subsequent to beta cell damage inflicted by a virus or toxins, production of anti-hHSP65 antibodies or anti-hHSP65 T-cells could enhance and perpetuate the process of beta cell destruction as the hHSP65 contained on the beta cells themselves will be attacked.

This reasoning helps to explain how induction of tolerance or suppression of an immune response to hHSP65 could prevent or cure the diabetic process even after it was initiated. Thus, hsp65, low molecular weight molecules (25, 30 or 47 KD) cross-reactive with hsp65, or fragments, modifed peptide sequences, synthetic peptides or even organic molecules based on the fusion-protein blueprint and designed so as to satisfy the physico-chemical requirements of hsp65, can be used to prevent or treat the IDDM process, as long as they are cross-reactive with polyclonal antibodies raised against hHSP65 or they raise antibodies which are cross-reactive with hHSP65.

The presence or incipience of IDDM can also be diagnosed by testing for the presence of any antibody that cross-reacts with hHSP65. Alternatively, this diagnosis can be made by testing for any protein which immunoreacts with an antibody against hHSP65.

As noted above, hsp65 is known to be associated with adjuvant arthritis in rats and with rheumatoid arthritis in humans. There would be no uncertainty regarding the assay of hsp65 or anti-hsp65 in discriminating between persons developing IDDM and those suffering from arthritis because, unlike the IDDM process, the process of arthritis is manifested clearly by blatant signs and symptoms of arthritis. Hence, detection of hsp65 or anti-hsp6without signs or symptoms of arthritis would serve to call attention to the possibility of subclinical beta cell destruction and incipient IDDM. Additional tests such as antibodies to beta cells could then be used to confirm a diagnosis of autoimmunity to beta cells.

The association of hsp90 with systemic lupus erythematosus (SLE) would also not be confused with the IDDM process because SLE is also characterized by clear signs and symptoms of illness, while the IDDM process is clinically silent.

The hsp65 can be used for the diagnosis of IDDM in which the hsp65 is injected subcutaneously into a patient, and the occurrence of a detectable skin reaction is observed. Alternatively, hsp65 is contacted with a patient's blood or blood component, and the occurrence of any immunological reaction with anti-hHSP65, i.e., any antibody which cross-reacts with hsp65, present in the patient's blood is detected by any known immunological method. Such well known immunological methods include radioimmunoassay, fluorescent immunoassay, ELISA, chemiluminescent assay, and the like.

In the in vivo skin test, the skin reaction at the site of the injection is measured after a sufficient time period, for example, 24 to 72 hours after administration. Swelling and/or redness is due to a delayed hypersensitivity-like reaction.

In the in vitro tests with blood or blood components, hsp65 is contacted, for example, with peripheral blood cells. Lymphocytes of positive patients are stimulated by hsp65 in that they will proliferate and/or produce biologically active factors, such as interleukins or products involved in the degradation of cartilage. Such reactions can be detected by methods well known in the art.

For the in vitro serological tests, serum of a patient is contacted with hsp65. If the serum contains antibodies against antigenic determinants of hsp65, an immunological reaction will occur which may be detected and assayed by means of standard techniques such as ELISA, agglutination, etc.

Any well known immunoassay technique can be used to detect the presence of hHSP65 or anti-hHSP65. It should be understood that once one of ordinary skill in the art becomes aware of the fact that the presence of anti-hHSP65 antibodies in the serum of a person, determined by means of assay with hsp65, is a positive indication of incipient or existing IDDM, such artisans would be well aware of the types of immunoassay technique which can be used. Besides radioimmunoassay (solid or liquid phase), any conventional immunoassay technique can be used, such as enzyme-linked immunosorbent assay (ELISA), heterogeneous immunoassay (both competitive and non-competitive) using labels other than enzymes and radioisotopes, homogeneous immunoassays based on fluorescence quenching and enzyme channeling, immune precipitation (including radial immune diffusion) and agglutination assays based on visual semi-quantitative detection or quantitative turbidimetric detection. The assay may use any conventional solid phase or sandwich assay techniques.

Similarly, kits may be prepared for carrying out any of the various assays used for accomplishing the present invention. Each such kit would include all of the materials necessary to conduct a single assay or a fixed number of assays. For example, such a kit for determining the presence of anti-hHSP65 antibodies may contain solid-phase immobilized hsp65 and a tagged antibody capable of recognizing the non-variable region of the anti-hHSP65 antibody to be detected, such as tagged anti-human Fab. A kit for determining the presence of hHSP65 may contain solid-phase immobilized antibody which reacts or cross-reacts with hHSP65, and a tagged antibody capable of reacting with a different epitope of hHSP65 than that recognized by the immobilized antibody. The kit should also contain reagent capable of precipitating immune complexes of hsp65 and anti-hHSP65 antibodies and may contain directions for using the kit and containers to hold the materials of the kit. Any conventional tag or label may be used, such as a radioisotope, an enzyme, a chromophore or a fluorophore. A typical radioisotope is iodine-125 or sulfur-35. Typical enzymes for this purpose include horseradish peroxidase, α-galactosidase and alkaline phosphatase.

The hsp65 can be used as immunogen in pharmaceutical compositions, particularly vaccines for the alleviation and treatment of IDDM, as well as antigens in diagnostic compositions for the diagnosis of IDDM. These pharmaceutical and diagnostic compositions, which may be prepared in a manner known in the art, also form part of the present invention.

Another way to improve the efficacy as a vaccine or therapeutic agent of the hsp65 is to construct, by known genetic engineering methods, microorganisms expressing the hsp65 either as such or as part of a fusion protein or as a multimer thereof. These microorganisms themselves can be used for the preparation of a live vaccine which will provoke not only the production of antibodies against the micro-organism in question, but will also be useful for the alleviation and treatment of IDDM. These genetically engineered microorganisms, and pharmaceutical compositions containing these, are also part of the present invention. Examples of suitable genetically engineered microorganisms are Vaccinia and Salmonella strains.

Diagnostic compositions according to the present invention are prepared by combining hsp65 with suitable adjuvants and auxiliary components.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A kit for diagnosing the presence or incipience of IDDM, comprising:

hHSP65;

a tagged antibody capable of recognizing the non-variable region of the anti-hHSP65 antibody to be detected; and means for conveying to the user that the kit is for use in the diagnosis of IDDM.

2. A kit in accordance with claim 1, wherein said hHSP65 is immobilized on a solid phase.

3. A kit in accordance with claim 1, wherein said means comprises instructions for use of the kit in the diagnosis of IDDM.

4. A kit in accordance with claim 1, wherein the tag is selected from the group consisting of radioisotopes, enzymes, chromophores, and fluorophores.

5. A kit for diagnosing the presence or incipience of IDDM, comprising:

antibodies reactive or cross-reactive with a first epitope of hHSP65;

a tagged antibody capable of recognizing an epitope of hHSP65 other than said first epitope; and means for conveying to the user that the kit is for use in the diagnosis of IDDM.

6. A kit in accordance with claim 5, wherein said antibodies reactive or cross-reactive with a first epitope of hHSP65 are immobilized on a solid phase.

7. A kit in accordance with claim 5, wherein said tagged antibody is tagged anti-human Fab.

8. A kit in accordance with claim 5, wherein the tag of said tagged antibody is selected from the group consisting of radioistopes, enzymes, chromophores, and fluorophores.

9. A kit in accordance with claim 5, wherein said means comprises instructions for use of the kit in the diagnosis of IDDM.

10. A kit for diagnosing the presence or incipience of IDDM, comprising:

hsp65;

a tagged antibody capable of recognizing the non-variable region of the antibody to be detected; and means for conveying to the user that the kit is for use in the diagnosis of IDDM.

11. A kit in accordance with claim 10, wherein said hsp65 is immobilized on a solid phase.

12. A kit in accordance with claim 10, wherein said means comprises instructions for use of the kit in the diagnosis of IDDM.

13. A kit in accordance with claim 10, wherein the tag is selected from the group consisting of radioisotopes, enzymes, chromophores, and fluorophores.

* * * * *